United States Patent [19]

Ikezaki et al.

[11] 4,276,304

[45] Jun. 30, 1981

[54] NOVEL BENZYLALCOHOL DERIVATIVE AND PROCESS FOR PREPARING THE SAME

[75] Inventors: Muneyoshi Ikezaki, Ageo; Katsuyuki Noguchi, Kitamoto; Hajime Iwai, Hasuda; Masanori Inamasu, Misato, all of Japan

[73] Assignee: Tanabe Seiyaku Co., Ltd., Osaka, Japan

[21] Appl. No.: 113,218

[22] Filed: Jan. 18, 1980

[30] Foreign Application Priority Data

Jan. 31, 1979 [JP] Japan .................................. 54-10562

[51] Int. Cl.³ ..................... C07C 91/34; A61K 31/135
[52] U.S. Cl. .............................. 424/282; 260/370.5 R; 260/501.17; 564/276; 564/361; 564/363; 564/365; 424/316; 424/330
[58] Field of Search ........ 260/570.6, 501.17, 340.5 R; 424/330, 282, 316; 564/361, 365, 363

[56] References Cited

U.S. PATENT DOCUMENTS

| 3,869,474 | 3/1975 | Miura | 260/343.7 |
| 4,032,575 | 6/1977 | Ikezaki | 260/570.6 |
| 4,131,686 | 12/1978 | Ikezaki | 424/330 |

FOREIGN PATENT DOCUMENTS 52-71428  6/1977  Japan ..................................... 260/570.6

Primary Examiner—Robert Gerstl
Attorney, Agent, or Firm—Bierman & Bierman

[57] ABSTRACT

A benzylalcohol derivative of the formula:

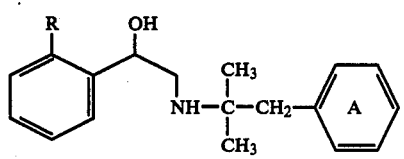

(I)

wherein R is hydroxy, benzyloxy, alkoxy of one to 4 carbon atoms or halogen, and Ring A is monomethoxyphenyl, dimethoxyphenyl, trimethoxyphenyl or 3,4-methylenedioxyphenyl is prepared by reducing a compound of the formula:

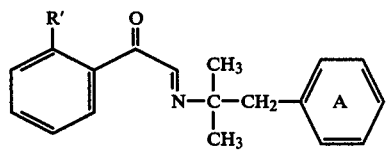

wherein R' is benzyloxy, alkoxy of one to 4 carbon atoms or halogen, and Ring A is the same as defined above, and when R' is benzyloxy, if required, further subjecting the product to catalytic hydrogenation.

The compounds (I) and pharmaceutically acceptable acid addition salts thereof are used as anti-diabetic agents.

36 Claims, No Drawings

NOVEL BENZYLALCOHOL DERIVATIVE AND PROCESS FOR PREPARING THE SAME

This invention relates to a novel benzylalcohol derivative and a process for preparing the same. More particularly, it relates to a compound of the formula:

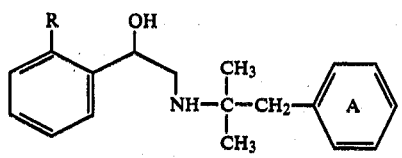

wherein R is hydroxy, benzyloxy, alkoxy of one to 4 carbon atoms or halogen, and Ring A is monomethoxyphenyl, dimethoxyphenyl, trimethoxyphenyl or 3,4-methylenedioxyphenyl, or a pharmaceutically acceptable acid addition salt thereof.

It is known that α-[(3,4-dimethoxyphenethylamino)-methyl]-2-hydroxybenzylalcohol, α-[(3,4-dimethoxyphenethylamino)methyl]-2-methoxybenzylalcohol and α-[(3,4-dimethoxyphenethylamino)methyl]-2-benzyloxybenzylalcohol show a blood sugar-lowering activity (cf. U.S. Pat. Nos. 4,032,575 and 4,131,686, and Japanese Patent Publication (unexamined) No. 71428/1977).

As a result of various investigations, we have now found that the benzylalcohol derivative (I) can induce remarkable decrease of blood sugar and is useful as an anti-diabetic agent. For example, when the blood sugar-lowering activity was estimated by orally administering a test compound to mice immediately before subcutaneous injection of glucose, said activity of the compound of the present invention was about 100 to about 1000 times stronger than that of Phenformin (Chemical name: 1-phenethylbiguanide).

The benzylalcohol derivative (I) may further show a preventive effect upon the aggregation of blood platelets and be used for treatment or prophylaxis of thrombosis, while α-[(3,4-dimethoxyphenethylamino)methyl]-2-hydroxybenzylalcohol and α-[(3,4-dimethoxyphenethylamino)methyl]-2-methoxybenzylalcohol disclosed in the aforementioned literatures show no substantial preventive effect upon aggregation of blood platelets. Moreover, the benzylalcohol derivative (I) shows no substantial adrenergic β-action such as the cardiac contractile action (one of the side effects of an anti-diabetic agent), and the acute toxicity thereof is also low. For example, the maximum tolerance dose (M.T.D.) of α-[(α,α-dimethyl-3,4-dimethoxyphenethylamino)methyl]-2-benzyloxybenzylalcohol oxalate and α-[(α,α-dimethyl-3,4-dimethoxyphenethylamino)-methyl]-2-chlorobenzylalcohol hydrochloride which was estimated 48 hours after intraperitoneal injection thereof to a group of 4 mice was not less than 100 mg/kg.

In the above-mentioned formula (I), representative examples of the group R include hydroxy; benzyloxy; alkoxy such as methoxy, ethoxy, propoxy and n-butoxy; and halogen such as chlorine and bromine. On the other hand, representative examples of Ring A include monomethoxyphenyl such as 2-methoxyphenyl, 3-methoxyphenyl and 4-methoxyphenyl; dimethoxyphenyl such as 2,3-dimethoxyphenyl and 3,4-dimethoxyphenyl; trimethoxyphenyl such as 2,3,4-trimethoxyphenyl and 3,4,5-trimethoxyphenyl; and 3,4-methylenedioxyphenyl. Among those of the invention, a preferred subgenus includes the compound of the formula (I) in which R is hydroxy, benzyloxy, methoxy, n-butoxy or chlorine, and Ring A is 4-methoxyphenyl, 3,4-dimethoxyphenyl, 2,3,4-trimethoxyphenyl or 3,4-methylenedioxyphenyl. Another preferred subgenus is the compound of the formula (I) in which R is hydrogen, benzyloxy, methoxy, n-butoxy or chlorine, and Ring A is 4-methoxyphenyl, 3,4-dimethoxyphenyl or 2,3,4-trimethoxyphenyl. Other preferred subgenus is the compound of the formula (I) in which R is benzyloxy, methoxy or chlorine, and Ring A is 4-methoxyphenyl, 3,4-dimethoxyphenyl or 2,3,4-trimethoxyphenyl. Further preferred subgenus is the compound of the formula (I) in which R is benzyloxy or chlorine, and Ring A is 3,4-dimethoxyphenyl.

According to the present invention, the compound (I) can be prepared by the steps of:

(i) condensing a phenylglyoxal derivative of the formula:

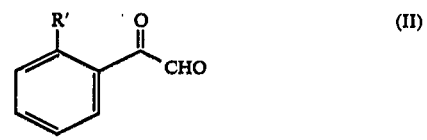

wherein R' is benzyloxy, alkoxy of one to 4 carbon atoms or halogen, or its hydrate with an α,α-dimethylphenethylamine derivative of the formula:

wherein Ring A is the same as defined above, to give an acetophenone derivative of the formula:

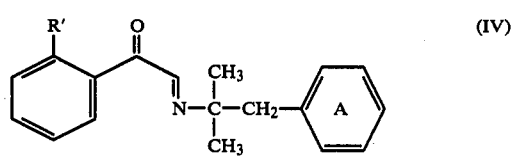

wherein R' and Ring A are the same as defined above, (ii) reducing the acetophenone derivative (IV) to give a benzylalcohol derivative of the formula:

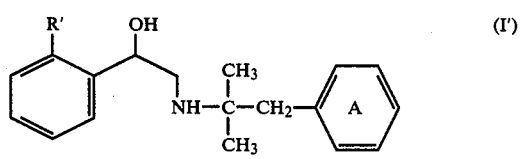

wherein R' and Ring A are the same as defined above. When R' is benzyloxy, said compound (I') may be, if required, further subjected to catalytic hydrogenation to give a benzylalcohol derivative of the formula:

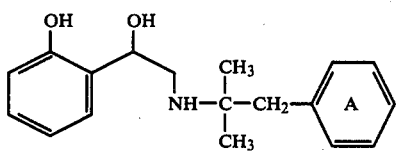

wherein Ring A is the same as defined above.

The starting compounds (II) and (III) can be readily prepared. For example, the compound (II) can be prepared by oxidizing an acetophenone derivative of the formula:

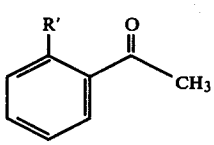

wherein R' is the same as defined above, with selenium dioxide.

On the other hand, the compound (III) can be prepared by reacting a benzaldehyde derivative of the formula:

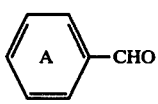

wherein Ring A is the same as defined above, with 2-nitropropane to give a 2-methyl-2-nitropropanol derivative of the formula:

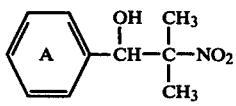

wherein Ring A is the same as defined above, reacting the 2-methyl-2-nitropropanol derivative with thionyl chloride to give a 1-chloro-2-methyl-2-nitropropane derivative of the formula:

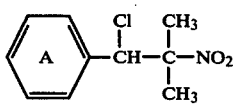

wherein Ring A is the same as defined above, and then subjecting the 1-chloro-2-methyl-2-nitropropane derivative to catalytic hydrogenation.

The condensation reaction of the phenylglyoxal derivative (II) or its hydrate with the α,α-dimethyl-phenethylamine derivative (III) can be readily accomplished. For example, the acetophenone derivative (IV) is prepared by admixing said starting compounds in the presence or absence of a catalyst in an inert solvent. Suitable examples of the solvent include, for example, dimethylsulfoxide and alkanol (e.g., methanol, ethanol, propanol). p-Toluenesulfonic acid is suitable as the catalyst. It is preferred to carry out the reaction at a temperature between 0° C. and 50° C. The acetphenone derivative (IV) thus obtained may be used in the subsequent reaction without isolating it from the reaction solution.

The benzylalcohol derivatie (I') is prepared by treating the compound (IV) with a reducing agent in an inert solvent. Suitable examples of the reducing agent include, for example, an alkali metal borohydride (e.g., sodium borohydride, potassium borohydride, lithium borohydride), lithium aluminium hydride, diborane and aluminium hydride. On the other hand, suitable examples of the solvent include, for example, tetrahydrofurane, dioxane, alkanol (e.g., methanol, ethanol, propanol) and a mixture of said alkanol and water or dimethylsulfoxide. It is preferred to carry out the reaction at a temperature between −10° C. and 50° C.

The benzylalcohol derivative (I') in which R' is benzyloxy may be, if required, further subjected to catalytic hydrogenation. Said catalytic hydrogenation may be conducted in the presence of a catalyst in an inert solvent. Suitable examples of the catalyst include, for example, platinum, platinum dioxide, palladium-black and palladium-carbon. Alkanol (e.g., methanol, ethanol, propanol) or a mixture of said alkanol and water is suitable as the solvent. It is preferred to carry out the reaction at a temperature between 20° C. and 50° C. It is also preferred to carry out the reaction under one to 5 atmospheric pressures.

The benzylalcohol derivative (I) of the present invention can be used for pharmaceutical use as either the free base or a pharmaceutically acceptable acid addition salt thereof. The base and salt thereof are readily convertible from one to the other by conventional methods, for example, by treating a solution of the free base with an acid or by neutralizing a solution of the acid addition salt with an alkali metal salt (e.g., potassium carbonate). Examples of the pharmaceutically acceptable acid addition salt include inorganic acid addition salts such as hydrochloride, phosphate, nitrate and sulfate, and organic acid addition salts such as acetate, lactate, tartrate, fumarate, maleate, oxalate, succinate, methanesulfonate and benzoate. The benzylalcohol derivative (I) may be administered either orally or parenterally, and may be further used in conjunction or admixture with a pharmaceutical exipient which is suitable for oral or parenteral administration. Th excipient selected must be one which does not react with the benzylalcohol derivative (I). Suitable excipients include, for example, gelatin, lactose, glucose, sodium chloride, starch, magnesium stearate, talcum, vegetable oil and benzylalcohol. The pharmaceutical preparation may be a solid dosage form such as pulvers, tablets and capsules, or a liquid dosage form such as a solution, an emulsion or a suspension. A daily dose of the benzylalcohol derivative (I) suitable for use as an anti-diabetic agent may be 1 μg to 10 mg, especially 5 μg to 5 mg, per kg of body weight.

Experiments

Blood sugar-lowering activity

An aqueous solution or suspension (10 ml/kg) of a test compound was administered orally through a stomach tube to a group of male ddY mice (each group consisting of five mice) which fasted for 20 hours. A physiological saline solution (10 ml/kg) containing 10 w/v % glucose was injected subcutaneously to the mice immediately after the oral administration of the test compound. One hour after the injection of glucose, 0.02 ml of blood was collected from the tail vein of the mice. Then, the amount of glucose in the blood sample was estimated by the glucose oxidase method (H. U. Bergmeyer & E. Bernt, "Methods of Enzymatic Analysis", H. U. Bergmeyer (Ed.), Acadamic Press, New York & London, 1963, page 123). The blood sugar-lowering activity of the test compound was calculated by the following formula:

Potency ratio =

$$\left[\frac{\left(\begin{array}{c}\text{Blood sugar level}\\\text{(mg/dl) in the}\\\text{control group}\end{array}\right) - \left(\begin{array}{c}\text{Blood sugar level}\\\text{(mg/dl) in the}\\\text{medicated group}\end{array}\right)}{\left(\begin{array}{c}\text{Blood sugar level}\\\text{(mg/dl) in the}\\\text{control group}\end{array}\right) - \left(\begin{array}{c}\text{Blood sugar level}\\\text{(mg/dl) in the group}\\\text{to which 100 mg/kg}\\\text{of Phenformin were}\\\text{administered}\end{array}\right)}\right] \times 100$$

(Note: Chemical name of Phenformin = 1-phenethylbiguanide)

Further, on the basis of the potency ratio calculated above, the activity of the test compound was expressed as follows:

| Potency ratio | Blood sugar-lowering activity |
|---|---|
| 0–33 | (−) |
| 34–66 | (±) |
| 67–150 | (+) |
| >150 | (++) |

Preventive effect upon the aggregation of blood platelets:

Blood was collected from the abdominal aorta of male Sprague-Dawley rats (body weight: 180–230 g) which were anesthetized with ether. Nine volumes of said blood were mixed with one volume of an aqueous 3.8% (w/v) trisodium citrate solution, and the mixture was centrifuged at 250×g for 5 minutes to give platelet-rich plasma (hereinafter referred to as "PRP") as the supernatant solution. The bottom layer was further centrifuged at 1000×g for 10 minutes to give platelet-poor plasma (hereinafter referred to as "PPP") as the supernatant slution. PRP was diluted with PPP so that the blood platelet count was $0.8$–$1 \times 10^6/\text{mm}^3$. Then, a mixture of 200 μl of said diluted PRP and 25 μl of a test compound solution (final concentration: 100 μg/ml) was introduced into a glass cell of SIENCO aggregometer (Sience Inc., Morrison, Colo., Model DP-247-D). After the mixture was stirred for 2 minutes at 37° C., 25 μl of a collagen solution which was prepared by the method of Holmsen et al. [Biochem. Biophys. Acta, 186, page 254(1969)] were added thereto, and the percentage inhibition of platelet aggregation was calculated from the degree of the platelet aggregation which was estimated by Born's method [Nature, 194, page 927(1969)]. Further, on the basis of said percentage inhibition calculated above, the platelet aggregation-inhibiting activity of the test compound was expressed as (−) if the test compound showed less than 10% inhibition of platelet aggregation; (+) if the test compound showed not less than 10% inhibition of platelet aggregation but said percentage inhibition was not higher than that of acetylsalicylic acid (100 μg/ml); or (++) if the test compound showed the platelet aggregation-inhibiting activity at least as strong as that of acetylsalicylic acid (100 μg/ml).

| Test compounds Nos. | Chemical name |
|---|---|
| (The compounds of the present invention) | |
| 1. | α-[(α,α-dimethyl-4-methoxyphenethylamino)-methyl]-2-hydroxybenzylalcohol ½ oxalate |
| 2. | α-[(α,α-dimethyl-4-methoxyphenethylamino)-methyl]-2-benzyloxybenzylalcohol (free base) |
| 3. | α-[(α,α-dimethyl-4-methoxyphenethylamino)-methyl]-2-methoxybenzylalcohol ½ oxalate |
| 4. | α-[(α,α-dimethyl-4-methoxyphenethylamino)-methyl]-2-n-butoxybenzylalcohol hydrochloride |
| 5. | α-[(α,α-dimethyl-4-metoxyphenethylamino)-methyl]-2-chlorobenzylalcohol hydrochloride |
| 6. | α-[(α,α-dimethyl-3,4-dimethoxyphenethylamino)-methyl]-2-hydroxybenzylalcohol ½ oxalate |
| 7. | α-[(α,α-dimethyl-3,4-dimethoxyphenethyl-amino)methyl]-2-benzyloxbenzylalcohol oxalate |
| 8. | α-[(α,α-dimethyl-3,4-dimethoxyphenethyl-amino)methyl]-2-methoxybenzylalcohol hydrochloride |
| 9. | α-[(α,α-dimethyl-3,4-dimethoxyphenethylamino)-methyl]-2-n-butoxybenzylalcohol hydrochloride |
| 10. | α-[(α,α-dimethyl-3,4-dimethoxyphenethylamino)-methyl]-2-chlorobenzylalcohol hydrochloride |
| 11. | α-[(α,α-dimethyl-2,3,4-trimethoxyphenethyl-amino)methyl]-2-hydroxybenzylalcohol ½ oxalate |
| 12. | α-[(α,α-dimethyl-2,3,4-trimethoxyphnethyl-amino)methyl]-2-benzyloxybenzylalcohol ½ oxalate |
| 13. | α-[(α,α-dimethyl-2,3,4-trimethoxyphenethyl-amino)methyl]-2-methoxybenzylalcohol hydrochloride |
| 14. | α-[(α,α-dimethyl-2,3,4-trimethoxyphenethyl-amino)methyl]-2-chlorobenzylalcohol hydrochloride |
| 15. | α-[(α,α-dimethyl-3,4-methylenedioxyphenethyl-amino)methyl]-2-hydroxybenzylalcohol ½ oxalate |
| 16. | α-[(α,α-dimethyl-3,4-methylenedioxyphenethyl-amino)methyl]-2-benzyloxybenzylalcohol ½ oxalate |
| 17. | α-[(α,α-dimethyl-3,4-methylenedioxyphenethyl-amino)methyl]-2-methoxybenzylalcohol ½ succinate |
| 18. | α-[(α,α-dimethyl-3,4-methylenedioxyphenethyl-amino)methyl]-2-n-butoxybenzylalcohol ½ oxalate |
| 19. | α-[(α,α-dimethyl-3,4-methylenedioxyphenethyl-amino)methyl]-2-chlorobenzylalcohol hydrochloride |
| (Known compounds) | |
| 20. | α-[(3,4-dimethoxyphenethylamino)methyl]-2-hydroxybenzylalcohol hydrochloride |
| 21. | α-[(3,4-dimethoxyphenethylamino)methyl]-2-methoxybenzylalcohol hydrochloride |

Results:

The results are shown in the following Tables 1 and 2.

TABLE 1

| Test Compound Nos. | (Blood sugar-lowering activity) Blood sugar-lowering activity (mg/kg) | | | | | | Minimum effective dose (mg/kg) |
|---|---|---|---|---|---|---|---|
| | 0.1 | 0.3 | 1.0 | 2.0 | 5.0 | 10.0 | |
| 1. | | − | + | + | | | 0.3 |
| 2. | | | − | + | + | | 1.0 |
| 3. | + | + | ++ | | | | 0.1 |
| 4. | ± | + | + | | | | 0.3 |
| 5. | + | + | ++ | | | | 0.1 |
| 6. | | − | ± | + | ++ | | 1.0 |
| 7. | | + | ++ | | | | 0.3 |

TABLE 1-continued (Blood sugar-lowering activity)

| Test Compound Nos. | Blood sugar-lowering activity (mg/kg) | | | | | | Minimum effective dose (mg/kg) |
| --- | --- | --- | --- | --- | --- | --- | --- |
| | 0.1 | 0.3 | 1.0 | 2.0 | 5.0 | 10.0 | |
| 8. | ± | + | ++ | | | | 0.3 |
| 9. | + | + | ++ | | | | 0.1 |
| 10. | ± | + | + | | | | 0.3 |
| 11. | − | + | + | + | | | 1.0 |
| 12. | − | + | + | | | | 1.0 |
| 13. | ± | + | + | | | | 1.0 |
| 14. | − | + | + | | | | 1.0 |
| 15. | − | + | + | | | | 1.0 |
| 16. | ± | + | ++ | | | | 1.0 |
| 17. | + | + | + | | | | 0.1 |
| 18. | | ± | + | + | | | 1.0 |
| 19. | ± | + | + | | | | 0.3 |
| (Known compounds) | | | | | | | |
| 20. | | | | − | + | + | 5.0 |
| 21. | | | − | + | + | ++ | 2.0 |

TABLE 2

(Platelet aggregation-inhibiting activity)

| Test Compound Nos. | Inhibition (%) against platelet aggregation (A*/B**) | Platelet aggregation inhibiting activity |
| --- | --- | --- |
| (The compounds of the present invention) | | |
| 1. | 90/39 | ++ |
| 2. | 27/31 | + |
| 3. | 80/39 | ++ |
| 6. | 57/58 | + |
| 7. | 90/50 | ++ |
| 8. | 22/56 | + |
| 9. | 31/39 | + |
| 10. | 17/56 | + |
| 11. | 67/39 | ++ |
| 12. | 57/39 | ++ |
| 13. | 84/39 | ++ |
| 14. | 33/47 | + |
| 15. | 85/50 | ++ |
| 16. | 59/39 | ++ |
| 17. | 93/50 | ++ |
| 18. | 37/39 | + |
| 19. | 29/50 | + |
| (Known compounds) | | |
| 20. | 2/56 | − |
| 21. | 6/54 | − |

Note:
A* : The inhibition (%) in the group to which each test compound (100 μg/ml) was added.
B** : The inhibition (%) in the group to which acetylsalicylic acid (100 μg/ml) was added.

EXAMPLE 1

(1) 11.5 g of sodium are added to 300 ml of anhydrous methanol, and 67 g of 4-methoxybenzaldehyde and 105 g of 2-nitropropane are added thereto at 13° C. for 25 minutes under stirring. The mixture is stirred at 23° C. for 70 hours. 32 g of acetic acid are added to the mixture under ice-cooling, and said mixture is evaporated under reduced pressure to remove solvent. About 200 ml of water are added to the residue, and the aqueous mixture is extracted with benzene. The extract is washed with a saturated sodium chloride solution, a saturated sodium bisulfite solution, water and a saturated sodium chloride solution, successively. The washed extract is dried and then evaporated to remove solvent. The residue (yellow oil, 65 g) is distilled at 75° C. under reduced pressure (1–2 mm Hg) to recover 47 g of the starting compound (i.e., 4-methoxybenzaldehyde). On the other hand, 14.5 g of 1-(4-methoxyphenyl)-2-methyl-2-nitropropanol (crude product) are obtained as the residue.

(2) A mixture of 14 g of 1-(4-methoxyphenyl)-2-methyl-2-nitropropanol (crude product) obtained in paragraph (1), 14.8 g of thionyl chloride and 140 ml of anhydrous benzene are refluxed for 1.5 hours. After the reaction, the reaction mixture is evaporated to remove solvent. The residue (dark brown oil. 16.5 g) is purified by silica gel chromatography (Solvent: n-hexane-ethyl acetate (10:1)). The resultant yellow oil (9.5 g) is crystallized with cold n-hexane, and then washed with cold petroleum ether. 7.2 g of 1-(4-methoxyphenyl)-1-chloro-2-methyl-2-nitropropane are thereby obtained as a white solid. M.p. 40°–41° C.

(3) A mixture of 812 mg of 1-(4-methoxyphenyl)-1-chloro-2-methyl-2-nitropropane, 2 ml of acetic acid, 150 mg of platinum dioxide and 20 ml of 1,2-dimethoxyethane is stirred at 20° C. for 2 hours in hydrogen gas atmosphere under 70 atmospheres, and then at 45° C. for 4.5 hours under 68–65 atmospheres, and then at 80° C. for 14 hours under 68 atmospheres. After cooling, the reaction mixture is filtered to remove insoluble materials, and said insoluble materials are washed with ethanol and water, successively. The filtrate and the washing are combined, and the combined solution is evaporated to remove solvent. Cold 10% hydrochloric acid is added to the residue (brown oil), and the mixture is extracted with chloroform. The aqueous layer is alkalized with 10% sodium hydroxide under cooling, and then extracted with benzene. The extract is washed with water and a saturated sodium chloride solution, successively. The washed extract is dried and then evaporated to remove solvent. The residue (colorless oil, 460 mg) is dissolved in 2 ml of isopropylalcohol. 4 ml of ether containing hydrogen chloride (27 g/500 ml) are added to the isopropylalcohol solution, and said solution is allowed to stand. The crystalline precipitates are collected by filtration, washed with ether, and then recrystallized from isopropylalcohol. 400 mg of α,α-dimethyl-4-methoxyphenethylamine hydrochloride are thereby obtained as colorless plates.
M.p. 165°–166° C.
Analysis calculated for $C_{11}H_{18}ONCl$: C, 61.25; H, 8.41; N, 6.49; Found: C, 61.24; H, 8.48; N, 6.41.

EXAMPLE 2

(1) 2.8 g of sodium are dissolved in 70 ml of anhydrous methanol, and 20 g of veratrumaldehyde and 26 g of 2-nitropropane are added thereto. The mixture is stirred at 20° C. for 18 hours. After the reaction, 5 ml of acetic acid are added to the reaction mixture, and said mixture is evaporated under reduced pressure to remove solvent. The residue is extracted with ether, and the extract is washed with water, a saturated sodium bisulfite solution, and a saturated sodium chloride solution. The washed extract is dried and then evaporated to remove solvent. 6.26 g of 1-(3,4-dimethoxyphenyl)-2-methyl-2-nitropropanol are thereby obtained as a brown oil.

IR$\nu_{max}^{CHCl_3}$ (cm$^{-1}$): 3580, 3380(b), 1600(sh), 1590, 1520(b), 1345

NMR (CDCl$_3$) ppm: 1.43 (s, CH$_3$, 3H), 1.58 (s, CH$_3$, 3H), 2.78 (s, OH, 1H), 3.86 (s, OCH$_3$×2, 6H), 5.22 (s, —CH(OH)—, 1H), 6.87 (s, aro—H, 3H)

Mass (m/e): 255 (M+), 209 (M+ −46), 167, 166, 139

(2) A mixture of 6.2 g of 1-(3,4-dimethoxyphenyl)-2-methyl-2-nitropropanol, 3 ml of thionyl chloride and 40 ml of anhydrous benzene is refluxed for 4 hours. After the reaction, the reaction mixture is evaporated to remove solvent. The residue (dark brown oil) is distilled at 145° C. under reduced pressure (0.15 mm Hg). 4.6 g of 1-(3,4-dimethoxyphenyl)-1-chloro-2-methyl-2-nitropropane are thereby obtained as pale yellow prisms.

M.p. 109°–110° C. (colorless prisms) (recrystallized from isopropyl ether)

IR $\nu_{max}^{nujol}$ (cm$^{-1}$): 1600, 1580, 1540(sh), 1535, 1340

NMR (CDCl$_3$) ppm: 1.51 (s, CH$_3$, 3H), 1.76 (s, CH$_3$, 3H), 3.9 (s, OCH$_3 \times 2$, 6H), 5.61 (s, —CH(Cl)—, 1H), 6.7–7.15 (m, aro—H, 3H)

Mass (m/e): 275 (M+2), 273(M+), 227, 192, 185 (base peak)

(3) A mixture of 3.6 g of 1-(3,4-dimethoxyphenyl)-1-chloro-2-methyl-2-nitropropane, 910 mg of sodium acetate, 6.7 ml of acetic acid, 200 mg of platinum dioxide, 280 mg of activated charcoal and 35 ml of 1,2-dimethoxyethane is shaken at 60°–85° C. for 5.5 hours in hydrogen gas atmosphere under 55 atmospheric pressures. After cooling, insoluble materials are removed by filtration, and the filtrate is evaporated under reduced pressure to remove solvent. The residue (pale yellow oil) is dissolved in water, and then washed with ether. The aqueous layer is neutralized with 20% sodium hydroxide under cooling, and then extracted with ether. The extract is washed with water, dried and then evaporated to remove solvent. The residue (colorless oil) is converted into its hydrochloride with hydrogen chlorideether, and said hydrochloride is recrystallized from isopropylalcohol. 2.1 g of α,α-dimethyl-3,4-dimethoxyphenethylamine hydrochloride are thereby obtained as colorless plates.

M.p. 232° 233° C.

IR $\nu_{max}^{nujol}$ (cm$^{-1}$): 2780, 2660, 2560, 2550, 1600, 1580, 1520

NMR (CDCl$_3$) ppm: (Free base) 1.08 and 1.11 (broad s, —C(CH$_3$)$_2$—, NH$_2$, 8H), 2.59 (s, Ar—CH$_2$—, 2H), 3.88 (s, OCH$_3 \times 2$, 6H), 6.6–6.9 (m, aro—H, 3H)

Mass (m/e): 209 (M+), 151, 58 (base peak)

Analysis calculated for C$_{12}$H$_{20}$NO$_2$Cl: C, 58.65; H, 8.20, N, 5.70; Found: C, 58.55; H, 8.08; N, 5.65.

EXAMPLE 3

(1) 6.4 g of sodium are added to 250 ml of anhydrous methanol, and 50 g of 2,3,4-trimethoxybenzaldehyde and 54.4 g of 2-nitropropane are added dropwise thereto at 15° C. for 40 minutes under stirring. The mixture is stirred at 25° C. for 24 hours, and 17 ml of acetic acid and 20 ml of methanol are added to said mixture under ice-cooling. The mixture is evaporated to remove solvent, and the residue is extracted with benzene. The extract is washed with water, an aqueous sodium bisulfite solution, water and a saturated sodium chloride solution, successively. The washed extract is dried and then evaporated to remove solvent. 63 g of 1-(2,3,4-trimethoxyphenyl)-2-methyl-2-nitropropanol are thereby obtained as a pale yellow oil.

(2) A mixture of 14.3 g of 1-(2,3,4-trimethoxyphenyl)-2-methyl-2-nitropropanol, 11.9 g of thionyl chloride and 150 ml of anhydrous benzene is refluxed for 3.5 hours. After the reaction, the reaction mixture is evaporated to remove solvent. The residue (yellow oil) is purified by silica gel chromatography (Solvent: n-hexane-ethyl acetate (10:1). 11.4 g of 1-(2,3,4-trimethoxyphenyl)-1-chloro-2-methyl-2-nitropropane are thereby obtained as a yellow oil.

NMR(CDCl$_3$) ppm: 1.6 (d, J=15 Hz, —C(CH$_3$)$_2$—, 6H), 3.87 (s, OCH$_3 \times 2$, 6H), 3.98 (s, OCH$_3$, 3H), 6.1 (s, —CH(Cl)—, 1H), 6.66 (d, J=15 Hz, Aro—H, 1H), 7.16 (d, J=15 Hz, Aro—H, 1H)

(3) A mixture of 5 g of 1-(2,3,4-trimethoxyphenyl)-1-chloro-2-methyl-2-nitropropane, 2 g of 10% palladium-carbon and 50 ml of ethanol is shaken at room temperature in hydrogen gas atmosphere under atmospheric pressure. After the uptake of hydrogen is completed, insoluble materials are removed by filtration, and the filtrate is evaporated to remove solvent. 3.95 g of 1-(2,3,4-trimethoxyphenyl)-2-methyl-2-nitropropane are thereby obtained as a yellow oil.

IR $\nu_{max}^{liq.}$ (cm$^{-1}$): 1600, 1550(sh), 1540, 1500

NMR (CDCl$_3$) ppm: 1.54 (s, —C(CH$_3$)$_2$—, 6H), 3.17 (s, Ar—CH$_2$—, 2H), 3.84 (d, OCH$_3 \times 3$, 9H), 6.44 (d, J=9 Hz, aro—H, 1H), 6.61 (d, J=9 Hz, aro—H, 1H)

(4) A mixture of 3.6 g of 1-(2,3,4-trimethoxyphenyl)-2-methyl-2-nitropropane, 400 mg of platinum dioxide, 35 ml of 1,2-dimethoxyethane and 1.5 ml of acetic acid is shaken at 65° C. for 15 hours in hydrogen gas atmosphere under 80 atmospheres. After cooling, the insoluble materials are removed by filtration. The filtrate is evaporated to remove solvent, and the residue (pale brown oil) is dissolved in ethyl acetate. The solution is washed with a saturated sodium bicarbonate solution and a saturated sodium chloride solution, dried and then evaporated to remove solvent. The residue (pale brown oil) thus obtained is distilled under reduced pressure, whereby 2.9 g of α,α-dimethyl-2,3,4-trimethoxyphenethylamine are obtained as a pale yellow oil.

B.p. (0.3 mm Hg) 133°–135° C.

Hydrochloride:

M.p. 206°–207° C. (recrystallized from a mixture of isopropylalcohol and isopropyl ether)

IR $\nu_{max}^{nujol}$ (cm$^{-1}$): 3250, 2800–2400, 1605, 1595, 1520, 1500

NMR (CDCl$_3$) ppm: 1.49 (s, —C(CH$_3$)$_2$—, 6H), 3.05 (s, Ar—CH$_2$—, 2H), 3.83 (s, OCH$_3$, 3H), 3.88 (s, OCH$_3$, 3H), 3.91 (s, OCH$_3$, 3H), 6.56 (d, J=8.5 Hz, aro—H, 1H), 6.92 (d, J=8.5 Hz, aro—H, 1H), 8.42 (b.s. NH$_2$)

Analysis calculated for C$_{13}$H$_{22}$NO$_3$Cl: C, 56.62; H, 8.04; N, 5.08; Found: C, 56.54; H, 8.13; N, 5.02.

EXAMPLE 4

(1) 7.7 g of sodium are added to 220 ml of anhydrous methanol, and 50 g of piperonal and 90 g of 2-nitropropane are added thereto. The mixture is stirred at room temperature for one hour, and then refluxed for 4 hours. After cooling, the reaction mixture is poured into ice-water containing 21 g of acetic acid, and then extracted with ether. The extract is washed with a saturated sodium chloride solution, a saturated sodium bisulfite solution and a saturated sodium chloride solution, successively. The washed extract is dried and then evaporated to remove solvent. 15 g of 1-(3,4-methylenedioxyphenyl)-2-methyl-2-nitropropanol are thereby obtained as a crude oil.

(2) A mixture of 15 g of 1-(3,4-methylenedioxyphenyl)-2-methyl-2-nitropropanol (crude oil), 12 g of thionyl chloride and 80 ml of anhydrous benzene is refluxed for 3 hours. After the reaction, the reaction mixture is evaporated to remove solvent and thionyl chloride. The residue is purified by silica gel chromatography (Solvent: benzene). 9.0 g of 1-(3,4-methylenedioxyphenyl)-1-chloro-2-methyl-2-nitropropane are thereby obtained as an oil.

NMR (CDCl$_3$) ppm: 1.50 (s, 3H), 1.74 (s, 3H), 5.52 (s, 1H), 5.99 (s, 2H), 6.7–7.0 (m, 3H)

(3) A mixture of 7.0 g of 1-(3,4-methylenedioxyphenyl)-1-chloro-2-methyl-2-nitropropane, 7.7 g of 70% perchloric acid, 2.8 g of 10% palladium-carbon and 100 ml of ethanol is shaken at room temperature for 3 hours in hydrogen gas atmosphere under 3 atmospheres. After the reaction, insoluble materials are removed by filtration, and the filtrate is condensed. The residue is dissolved in ethyl acetate, and the solution is washed with water, a saturated sodium bicarbonate solution and a saturated sodium chloride solution, successively. The washed solution is dried and then evaporated to remove solvent. 5.4 g of 1-(3,4-methylenedioxyphenyl)-2-methyl-2-nitropropane are thereby obtained as an oil.

NMR (CDCl$_3$) ppm: 1.57 (s, 6H), 3.12 (s, 2H), 5.96 (s, 2H), 6.3–6.8 (m, 3H)

Mass (m/e): 223 (M+), 177, 135

(4) A mixture of 0.8 g of 1-(3,4-methylenedioxyphenyl)-2-methyl-2-nitropropane, 100 mg of platinum dioxide, one ml of acetic acid and 20 ml of 1,2-dimethoxyethane is shaken at 60°–70° C. for 18 hours in hydrogen gas atmosphere under elevated pressure (initial pressure: 80 atmospheric pressures). After the reaction, the insoluble materials are removed by filtration, and the filtrate is evaporated to remove solvent. The residue is dissolved in ethyl acetate, and the solution is extracted with 5% hydrochloric acid. The extract is alkalized with potassium carbonate, and then extracted with ethyl acetate. The extract is washed with a saturated sodium chloride solution, dried and then evaporated to remove solvent. The residue (oil) is distilled at 100°–120° C. (bath temperature) under reduced pressure (0.04 mm Hg). 0.5 g of α,α-dimethyl-3,4-methylenedioxyphenethylamine are thereby obtained as an oil.

NMR (CDCl$_3$) ppm: 1.10 (s, 6H), 1.22 (s, 2H), 2.57 (s, 2H), 5.92 (s, 2H), 6.45–6.90 (m, 3H)

Hydrochloride:

M.p. 163°–164° C. (recrystallized from a mixture of ethanol and ether)

Analysis calculated for C$_{11}$H$_{16}$O$_2$NCl: C, 57.51; H, 7.02; N, 6.10; Found: C, 57.39; H, 6.96; N, 6.17.

EXAMPLE 5

(1) A mixture of 928 mg of 2-chloroacetophenone, 866 mg of selenium dioxide, 8 ml of 1,4-dioxane and 0.4 ml of water is refluxed for 7 hours. After cooling, the precipitates are collected by filtration, and then washed with benzene. The filtrate and the washing are combined, and the combined solution is evaporated to remove solvent. The residue is dissolved in benzene, and the solution is washed with a saturated sodium chloride solution, a saturated sodium bicarbonate solution and a saturated sodium chloride solution, successively. The washed solution is dried and then evaporated to remove solvent. 835 mg of 2-chlorophenylglyoxal hydrate are thereby obtained as a yellow oil.

(2) 419 mg of 2-chlorophenylglyoxal hydrate are dissolved in 0.5 ml of dimethylsulfoxide, and a solution of 400 mg of α,α-dimethyl-4-methoxyphenethylamine in 0.5 ml of dimethylsulfoxide is added thereto. The solution is stirred at 20° C. for one hour, whereby a solution of α-(α,α-dimethyl-4-methoxyphenethylimino)-2-chloroacetophenone in dimethylsulfoxide is obtained.

(3) 10 ml of ethanol are added to the α-(α,α-dimethyl-4-methoxyphenethylimino)-2-chloroacetophenone solution obtained in paragraph (2), and the mixture is stirred at 20° C. for 30 minutes. 127 mg of sodium borohydride are added to the mixture, and said mixture is stirred at 20° C. for 2.5 hours. After the reaction, the reaction mixture is evaporated to remove solvent. The residue is extracted with chloroform, and the extract is washed with water, 10% hydrochloric acid, water and a saturated sodium chloride solution, successively. The washed extract is dried and then evaporated to remove solvent. The residue (yellow oil) is crystallized with a mixture of isopropyl ether and ethyl acetate, and the resultant white solid (580 mg) is recrystallized from a mixture of ethanol and ether (1:3). 490 mg of α-[(α,α-dimethyl-4-methoxyphenethylamino)-methyl]-2-chlorobenzylalcohol hydrochloride are thereby obtained as colorless prisms.

M.p. 170°–171° C.

Analysis calculated for C$_{19}$H$_{25}$O$_2$NCl: C, 61.63; H, 6.81; N, 3.78; Found: C, 61.76; H, 6.84; N, 3.90.

EXAMPLE 6

(1) A mixture of 750 mg of 2-methoxyacetophenone, 722 mg of selenium dioxide, 8 ml of 1,4-dioxane and 0.3 ml of water is refluxed for 6 hours. After cooling, the precipitates are collected by filtration, and then washed with benzene. The filtrate and the washing are combined, and the combined solution is evaporated to remove solvent. The residue (orange yellow oil) is dissolved in benzene, and the solution is washed with a saturated sodium chloride solution, a saturated sodium bicarbonate solution and a saturated sodium chloride solution, successively. The washed solution is dried and then evaporated to remove solvent. 554 mg of 2-methoxyphenylglyoxal hydrate are thereby obtained as a yellow oil.

(2) 434 mg of 2-methoxyphenylglyoxal hydrate are dissolved in 0.5 ml of dimethylsulfoxide, and a solution of 427 mg of α,α-dimethyl-4-methoxyphenethylamine in 1.5 ml of dimethylsulfoxide is added thereto. The mixture is stirred at 20° C. for one hour, whereby a solution of α-(α,α-dimethyl-4-methoxyphenethylimino)-2-methoxyacetophenone in dimethylsulfoxide is obtained.

(3) 10 ml of ethanol are added to the α-(α,α-dimethyl-4-methoxyphenethylimino)-2-methoxyacetophenone solution obtained in paragraph (2), and the mixture is stirred at 20° C. for 30 minutes. 136 mg of sodium borohydride are added to the mixture, and said mixture is stirred at 20° C. for 2.5 hours. After the reaction, the reaction mixture is evaporated to remove the solvent. The residue (red orange oil) is extracted with chloroform, and the extract is washed with water, 10% hydrochloride acid, water, 10% sodium hydroxide solution and water, successively. The washed extract is dried and then evaporated to remove the solvent, whereby 770 mg of a pale yellow oil are obtained. 630 mg of said oil are dissolved in ether, and a solution of 86 mg of oxalic acid in ether is added thereto. The resultant white solid (620 mg) is recrystallized from methanol. 470 mg of α-[(α,α-dimethyl-4-methoxyphenethylamino)methyl]-2-methoxybenzylalcohol ½ oxalate are thereby obtained as colorless needles.

M.p. 216°–217° C. (decomp.)

Analysis calculated for C$_{21}$H$_{28}$O$_5$N. C, 67.34; H, 7.54; N, 3.74; Found: C, 67.40; H, 7.41; N, 3.77.

EXAMPLE 7

(1) A mixture of 1.25 g of 2-benzyloxyacetophenone, 0.8 g of selenium dioxide, 12 ml of 1,4-dioxane and 0.5 ml of water is refluxed for 15 hours. After cooling, the precipitates are collected by filtration, and then washed with benzene. The filtrate and the washing are combined, and the combined solution is evaporated to remove the solvent. The residue (orange yellow oil) is dissolved in benzene, and the solution is washed with water, a saturated sodium bicarbonate solution, water and a saturated sodium chloride solution, successively. The washed solution is dried and then evaporated to remove the solvent. 1.28 g of 2-benzyloxyphenylglyoxal hydrate are obtained as a yellow oil.

(2) 1.16 g of 2-benzyloxyphenylglyoxal hydrate are dissolved in one ml of dimethylsulfoxide, and a solution of 0.78 g of α,α-dimethyl-4-methoxyphenethylamine in 1.5 ml of dimethylsulfoxide is added thereto. The mixture is stirred at 23° C. for one hour, whereby a solution of α-(α,α-dimethyl-4-methoxyphenethylimino)-2-benzyloxyacetophenone in dimethylsulfoxide is obtained.

(3) 14 ml of ethanol are added to the α-(α,α-dimethyl-4-methoxyphenethylimino)-2-benzyloxyacetophenone solution obtained in paragraph (2), and the mixture is stirred at 23° C. for one hour. 248 mg of sodium borohydride are added to the mixture under cooling, and said mixture is stirred at 20° C. for 2 hours. After the reaction, the reaction mixture is evaporated to remove the solvent. The residue (yellow oil) is dissolved in ethyl acetate, and the solution is washed with water, 10% hydrochloric acid, water and a saturated sodium chloride solution, successively. The washed solution is dried and then evaporated to remove the solvent. The residue (pale yellow oil) is crystallized with a mixture of isopropyl ether and benzene, and the resultant white solid (1.74 g) is recrystallized from a mixture of isopropyl ether and isopropylalcohol (2:3). 1.5 g of α-[(α,α-dimethyl-4-methoxyphenethylamino)methyl]-2-benzyloxybenzylalcohol hydrochloride are thereby obtained as colorless prisms.

M.p. 128°–129° C.
Free base:
M.p. 91°–92° C. (recrystallized from isopropyl ether)
Analysis calculated for $C_{26}H_{31}O_3N$: C, 77.00; H, 7.71; N, 3.45; Found: C, 76.97; H, 7.76; N, 3.54.

EXAMPLE 8

A mixture of 442 mg of α-[(α,α-dimethyl-4-methoxyphenethylamino)methyl]-2-benzyloxybenzylalcohol hydrochloride, 250 mg of 10% palladium-carbon and 25 ml of 95% aqueous ethanol is shaken at room temperature in hydrogen gas atmosphere under atmospheric pressure. After the uptake of hydrogen is completed, insoluble materials are removed by filtration. The filtrate is evaporated to remove the solvent. The residue (colorless oil) is alkalized with an aqueous ammonia solution, whereby 300 mg of a pale yellow oil are obtained. Said oil is converted into its oxalate by using 45 mg of oxalic acid, and the oxalate is recrystallized from 95% aqueous methanol. 243 mg of α-[(α,α-dimethyl-4-methoxyphenethylamino)methyl]-2-hydroxybenzylalcohol ½ oxalate are thereby obtained as colorless needles.

M.p. 224°–225° C. (decomp.)
Analysis calculated for $C_{20}H_{26}O_5N$: C, 66.65; H, 7.27; N, 3.89; Found: C, 66.62; H, 7.25; N, 4.05.

EXAMPLE 9

(1) A mixture of 960 mg of 2-n-butoxyacetophenone, 700 mg of selenium dioxide, 10 ml of 1,4-dioxane and 0.5 ml of water is refluxed for 6 hours. After cooling, the precipitates are collected by filtration, and then washed with benzene. The filtrate and the washing are combined, and the combined solution is evaporated to remove the solvent. The residue (orange yellow oil) is dissolved in benzene, and the solution is washed with a saturated sodium chloride solution, a saturated sodium bicarbonate solution and a saturated sodium chloride solution, successively. The washed solution is dried and then evaporated to remove the solvent. One g of 2-n-butoxyphenylglyoxal hydrate is thereby obtained as an orange yellow oil.

(2) 632 mg of 2-n-butoxyphenylglyoxal hydrate are dissolved in 0.5 ml of dimethylsulfoxide, and a solution of 440 mg of α,α-dimethyl-4-methoxyphenethylamine in 1.5 ml of dimethylsulfoxide is added thereto. The mixture is stirred at 20° C. for one hour, whereby a solution of α-(α,α-dimethyl-4-methoxyphenethylimino)-2-n-butoxyacetophenone in dimethylsulfoxide is obtained.

(3) 10 ml of ethanol are added to the α-(α,α-dimethyl-4-methoxyphenethylimino)-2-n-butoxyacetophenone solution obtained in paragraph (2), and the mixture is stirred at 20° C. for 30 minutes. 140 mg of sodium borohydride are added to the mixture, and said mixture is stirred at 20° C. for 2 hours. After the reaction, the reaction mixture is evaporated to remove the solvent. The residue (red brown oil) is dissolved in ethyl acetate, and the solution is washed with a saturated sodium chloride solution, water, 10% hydrochloric acid, water and a saturated sodium chloride solution, successively. The washed solution is dried and then evaporated to remove the solvent. The residue (yellow oil) thus obtained is crystallized with a mixture of isopropyl ether and benzene, and the resultant white solid (620 mg) is recrystallized from a mixture of isopropylalcohol and isopropyl ether (1:3). 540 mg of α-[(α,α-dimethyl-4-methoxyphenethylamino)methyl]-2-n-butoxybenzylalcohol hydrochloride are thereby obtained as colorless prisms.

M.p. 120°–121° C.
Analysis calculated for $C_{23}H_{34}O_3NCl$: C, 67.71; H, 8.40; N, 3.43; Found: C, 67.92; H, 8.35; N, 3.50.

EXAMPLE 10

(1) 570 mg of 2-benzyloxyphenylglyoxal hydrate are dissolved in 0.5 ml of dimethylsulfoxide, and a solution of 450 mg of α,α-dimethyl-3,4-dimethoxyphenethylamine in 0.7 ml of dimethylsufoxide is added thereto. The mixture is stirred at 20° C. for 2 hours, whereby a solution of α-(α,α-dimethyl-3,4-dimethoxyphenethylimino)-2-benzyloxyacetophenone in dimethylsufoxide is obtained.

(2) 5 ml of ethanol are added to the α-(α,α-dimethyl-3,4-dimethoxyphenethylimino)-2-benzyloxyacetophenone solution obtained in paragraph (1), and the mixture is stirred at 20° C. for one hour. 140 mg of sodium borohydride are added to the mixture under ice-cooling, and said mixture is stirred at 20° C. for 3 hours. After the reaction, the reaction mixture is evaporated to remove solvent. The residue is dissolved in ethyl acetate, and the solution is washed with water, 10% hydrochloric acid and water, successively. The washed solution is dried and then evaporated. The residue (pale yellow caramel, 950 mg) thus obtained is alkalized with an aqueous ammonia solution under cooling, and then extracted with ether. The extract is evaporated to remove solvent. The residue (pale yellow oil, 890 mg) thus obtaned is dissolved in ether, and a solution of 221 mg of oxalic acid in acetone is added thereto. The crystalline precipitates are collected by filtration, washed with a mixture of acetone and ether, and the resultant crystals (910 mg) are recrystallized from isopropylalcohol. 495 mg of α-[(α,α-dimethyl-3,4-dimethoxyphenethylamino)methyl]-2-benzyloxybenzylalcohol oxalate are thereby obtained as colorless prisms.

M.p. 157°–158° C.

Mass (m/e): 284, 266, 222, 193, 151, 91 (base peak)

Analysis calculated for $C_{29}H_{35}NO_8$: C, 66.27; H, 6.71; N, 2.67; Found: C, 66.47; H, 6.79; N, 2.69.

On the other hand, the mother liquor obtained after isolation of the above-metntioned oxalate is condensed, whereby 98 mg of α-[(α,α-dimethyl-3,4-dimethoxyphenethylamino)methyl]-2-benzyloxybenzylalcohol ½ oxalate are obtained as colorless cubes.

M.p. 172°–173° C.

Mass (m/e): This product shows the same pattern as that of the above-mentioned 1 oxalate.

Analysis calculated for $C_{28}H_{34}NO_6$: C, 69.99; N, 7.13; N, 2.92; Found: C, 69.84; N, 7.08; N, 2.94.

Free base:

M.p. 144°–145° C. (recrystallized from isopropylalcohol)

EXAMPLE 11

A mixture of 263 mg of α-[(α,α-dimethyl-3,4-dimethoxyphenethylamino)methyl]-2-benzyloxybenzylalcohol oxalate (M.p. 157°–158° C.), 150 mg of 10% palladium-carbon and 15 ml of 95% aqueous ethanol is shaken at 20° C. in hydrogen gas atmosphere under atmospheric pressure. After the uptake of hydrogen is completed, insoluble materials are removed by filtration. The filtrate is evaporated to remove the solvent. The residue (colorless oil) is crystallized with a mixture of acetone and ether, and then recrystallized from isopropylalcohol. 180 mg of α-[(α,α-dimethyl-3,4-dimethoxyphenethylamino)methyl]-2-hydroxybenzylalcohol ½ oxalate are thereby obtained as colorless prisms.

M.p. 187°–188° C.

$IR\nu_{max}^{nujol}$ ($cm^{-1}$): 3300 (broad), 2800–2300, 1590, 1510

Mass (m/e): 222, 194, 176, 151

Analysis calculated for $C_{21}H_{28}NO_6$: C, 64.60; H, 7.23; N, 3.59; Found: C, 64.44; H, 7.29; N, 3.56.

EXAMPLE 12

(1) 645 mg of 2-methoxyphenylglyoxal hydrate are dissolved in one ml of dimethylsulfoxide, and a solution of 826 mg of α,α-dimethyl-3,4-dimethoxyphenethylamine in 1.5 ml of dimethylsulfoxide is added thereto. The mixture is stirred at 25° C. for one hour, whereby a solution of α-(α,α-dimethyl-3,4-dimethoxyphenethylimino)-2-methoxyacetophenone in dimethylsulfoxide is obtained.

(2) 10 ml of ethanol are added to the α-(α,α-dimethyl-3,4-dimethoxyphenethylimino)-2-methoxyacetophenone solution obtained in paragraph (1), and the mixture is stirred at 25° C. for 30 minutes. 225 mg of sodium borohydride are added to the mixture under cooling, and said mixture is stirred at 25° C. for 2 hours. After the reaction, the reaction mixture is evaporated to remove the solvent, and the residue is extracted with chloroform. The extract is washed with water, 10% hydrochloric acid, water and a saturated sodium chloride solution, successively. The washed extract is dried and then evaporated to remove the solvent. The residue (yellow oil) thus obtained is crystallized with a mixture of ethyl acetate and isopropyl ether (1:3), and the resultant white solid (1.33 g) is recrystallized from isopropylalcohol. 940 mg of α-[(α,α-dimethyl-3,4-dimethoxyphenethylamino)methyl]-2-methoxybenzylalcohol hydrochloride are obtained as colorless prisms.

M.p. 173°–174° C.

Analysis calculated for $C_{21}H_{30}O_4NCl$: C, 63.71; H, 7.64; N, 3.54; Found: C, 63.93; H, 7.56; N, 3.58.

EXAMPLE 13

(1) 625 mg of 2-chlorophenylglyoxal hydrate are dissolved in one ml of dimethylsulfoxide, and a solution of 696 mg of α,α-dimethyl-3,4-dimethoxyphenethylamine in 1.7 ml of dimethylsulfoxide is added thereto. The mixture is stirred at 25° C. for one hour, whereby a solution of α-(α,α-dimethyl-3,4-dimethoxyphenethylimino)-2-chloroacetophenone in dimethylsulfoxide is obtained.

(2) 10 ml of ethanol are added to the α-(α,α-dimethyl-3,4-dimethoxyphenethylimino)-2-chloroacetophenone solution obtained in paragraph (1), and the mixture is stirred at 25° C. for 30 minutes. 211 mg of sodium borohydride are added to the mixture under cooling, and said mixture is stirred at 25° C. for 2 hours. After the reaction, the reaction mixture is evaporated to remove the solvent. The residue (yellow oil) is dissolved in chloroform, and the solution is washed with a saturated sodium chloride solution, water, 10% hydrochloric acid and a saturated sodium chloride solution, successibely. The washed soluton is dried and then evaporated to remove the solvent. The residue (pale yellow oil) thus obtained is crystallized with a mixture of isopropyl ether and ethyl acetate, and the resultant white solid (1 g) is recrystallized from isopropylalcohol. 890 mg of α-[(α,α-dimethyl-3,4-dimethoxyphenethylamino)methyl]-2-chlorobenzylalcohol hydrochloride are thereby obtained as colorless prisms.

M.p. 180°–181° C.

Analysis calculated for $C_{20}H_{27}O_3NCl_2$: C, 60.00; H, 6.80; N, 3.50; Found: C, 60.21; H, 6.58; N, 3.55.

EXAMPLE 14

(1) 2 g of 2-n-butoxyphenylglyoxal hydrate are dissolved in 2.5 ml of dimethylsulfoxide, and a solution of 1.83 g of α,α-dimethyl-3,4-dimethoxyphenethylamine in one ml of dimethylsulfoxide is added thereto. The mixture is stirred at 25° C. for 30 minutes, whereby a solution of α-(α,α-dimethyl-3,4-dimethoxyphenethylimino)-2-n-butoxyacetophenone in dimethylsulfoxide is obtained.

(2) 15 ml of ethanol are added to the α-(α,α-dimethyl-3,4-dimethoxyphenethylimino)-2-n-butoxyacetophenone solution obtained in paragraph (1), and the mixture is stirred at 25° C. for 30 minutes. 0.5 g of sodium borohydride are added to the mixture under cooling, and said mixture is stirred at 25° C. for 2 hours. After the reaction, the reaction mixture is evaporated to remove solvent. The residue (yellow oil) is dissolved in chloroform, and the solution is washed with water, 10% hydrochloric acid and water, successively. The washed solution is dried and then evaporated to remove solvent. The residue thus obtained is crystallized with a mixture of isopropyl ether and ethyl acetate, and the resultant white solid (2.96 g) is recrystallized from ethyl acetate. 2.76 g of α-[(α,α-dimethyl-3,4-dimethoxyphenethylamino)methyl]-2-n-butoxybenzylalcohol hydrochloride are thereby obtained as colorless prisms.

M.p. 137°–138° C.

Analysis calculated for $C_{24}H_{36}O_4NCl$: C, 65.81; H, 8.29; N, 3.20; Found: C, 65.68; H, 8.21; N, 3.26.

EXAMPLE 15

(1) 2.4 g of 2-benzyloxyphenylglyoxal hydrate are dissolved in 3 ml of dimethylsulfoxide, and a solution of 1.9 g of α,α-dimethyl-2,3,4-trimethoxyphenethylamine in 5 ml of dimethylsulfoxide is added thereto. The mixture is stirred at 25° C. for one hour, whereby a solution of α-(α,α-dimethyl-2,3,4-trimethoxyphenethylimino)-2-benzyloxyacetophenone in dimethylsulfoxide is obtained.

(2) 20 ml of ethanol are added to the α-(α,α-dimethyl-2,3,4-trimethoxyphenethylimino)-2-benzyloxyacetophenone solution obtained in paragraph (1), and the mixture is stirred at 25° C. for 30 minutes. 453 mg of sodium borohydride are added to the mixture under ice-cooling, and said mixture is stirred at 25° C. for 2 hours. After the reaction, the reaction mixture is evaporated to remove the solvent, and the residue is extracted with ethyl acetate. The extract is washed with water, 10% hydrochloric acid, water and a saturated sodium chloride solution, successively. The washed extract is dried and then evaporated to remove the solvent. The residue (yellow oil) is converted into its free base by using an aqueous ammonia solution, and said free base is further converted into its oxalate. The resultant white solid (4 g) is recrystallized from methanol, whereby 3.8 g of α-[(α,α-dimethyl-2,3,4-trimethoxyphenethylamino)methyl]-2-benzyloxybenzylalcohol ½ oxalate are obtained as colorless prisms.

M.p. 197°–198° C. (decomp.)

Analysis calculated for $C_{29}H_{36}NO_7$: C, 68.22; H, 7.10; N, 2.74; Found: C, 68.25; H, 6.92; N, 3.05.

IR$\nu_{max}^{nujol}$ (cm$^{-1}$): 3180, 3050(sh), 2850–2250, 1630, 1595, 1500

NMR (DMSO-d$_6$) ppm: 1.03 (s, —C(CH$_3$)$_2$—, 6H), 2.75 (s, Ar—CH$_2$—, 2H), 3.74, 3.75 (s, OCH$_3$×3, 9H), 5.12 (s, Ph—CH$_2$O—, 2H), 5.15–5.4 (m, —CH(OH)—, 1H), 6.5–7.7 (m, aro—H, 11H)

EXAMPLE 16

A mixture of 1.53 g of α-[(α,α-dimethyl-2,3,4-trimethoxyphenethylamino)methyl]-2-benzyloxybenzylalcohol ½ oxalate, 500 mg of 10% palladium-carbon, 100 ml of ethanol and 5 ml of water is shaken at room temperature in hydrogen gas atmosphere under atmospheric pressure. After the uptake of hydrogen is completed, 300 ml of methanol are added to the reaction mixture. Insoluble materials are removed by filtration under heating, and then washed with hot methanol. The filtrate and the washing are combined, and the combined solution is evaporated to remove the solvent. The resultant white solid is recrystallized from methanol. One g of α-[(α,α-dimethyl-2,3,4-trimethoxyphenethylamino)methyl]-2-hydroxybenzylalcohol ½ oxalate is obtained as colorless prisms.

M.p. 225°–226° C. (decomp.)

Analysis calculated for $C_{22}H_{30}NO_7$: C, 62.84; H, 7.19; N, 3.33; Found: C, 62.76; H, 7.25; N, 3.42.

IR$\nu_{max}^{nujol}$ (cm$^{-1}$): 3450 –3100(b), 2750 –2300(b) 1600, 1580, 1570

NMR (CDCl$_3$) ppm: (Free base) 1.06 (s, —C(CH$_3$)$_2$—, 6H), 2.68 (s, Ar—CH$_2$—, 2H), 2.97 (b.t, J=5.3 Hz, —CH$_2$—N, 2H), 3.83 (s, OCH$_3$×3, 9H), 4.76 (b.t, J=4.8 Hz, —C$\underline{H}$(OH)—, 1H), 5.92 (b.s, NH, OH×2, 3H), 6.4–7.3 (m, aro—H, 6H)

EXAMPLE 17

(1) 180 mg of 2-chlorophenylglyoxal hydrate are dissolved in 2 ml of dimethylsulfoxide, and 217 mg of α,α-dimethyl-2,3,4-trimethoxyphenethylamine are added thereto. The mixture is stirred at 20° C. for one hour, whereby a solution of α-(α,α-dimethyl-2,3,4-trimethoxyphenethylimino)-2-chloroacetophenone in dimethylsulfoxide is obtained.

(2) 8 ml of ethanol are added to the α-(α,α-dimethyl-2,3,4-trimethoxyphenethylimino)-2-chloroacetophenone solution obtained in paragraph (1), and the mixture is stirred at 20° C. for 30 minutes. 52 mg of sodium borohydride are added to the mixture, and said mixture is stirred at 20° C. for 2 hours. After the reaction, the reaction mixture is evaporated to remove the solvent. The residue is extracted with ethyl acetate, and the extract is washed with a saturated sodium chloride solution, water, 10% hydrochloric acid, water and a saturated sodium chloride solution, successively. The washed solution is dried and then evaporated to remove the solvent. The residue thus obtained is washed with ethyl acetate, and the resultant white solid (200 mg) is recrystallized from a mixture of ethanol and ether (1:1). 160 mg of α-[(α,α-dimethyl-2,3,4-trimethoxyphenethylamino)methyl]-2-chlorobenzylalcohol hydrochloride are thereby obtained as colorless prisms.

M.p. 197°–198° C.

Analysis calculated for $C_{21}H_{29}O_4NCl_2$:

C, 58.61; H, 6.79; N, 3.26; Found: C, 58.56; H, 6.71; N, 3.36.

EXAMPLE 18

(1) A solution of 133 mg of α,α-dimethyl-2,3,4-trimethoxyphenethylamine in 1.5 ml of dimethylsulfoxide is added to 111 mg of 2-methoxyphenylglyoxal hydrate, and the mixture is stirred at 20° C. for one hour, whereby a solution of α-(α,α-dimethyl-2,3,4-trimethoxyphenethylimino)-2-methoxyacetophenone in dimethylsulfoxide is obtained.

(2) 8 ml of ethanol are added to the α-(α,α-dimethyl-2,3,4-trimethoxyphenethylimino)-2-methoxyacetophenone solution obtained in paragraph (1), and the mixture is stirred at 20° C. for 30 minutes. 33 mg of sodium borohydride are added to the mixture, and said mixture is stirred at 20° C. for 2 hours. After the reaction, the reaction mixture is evaporated to remove the solvent. The residue is extracted with ethyl acetate, and the extract is washed with a saturated sodium chloride solution, water, 10% hydrochloric acid, water and a saturated sodium chloride solution, successively. The washed extract is dried and then evaporated to remove the solvent. The residue (yellow oil, 120 mg) is crystallized with a mixture of isopropyl ether and isopropylalcohol, and the resultant white solid (87 mg) is recrystallized from a mixture of ethanol and ether (1:3). 63 mg of α-[(α,α-dimethyl-2,3,4-trimethoxyphenethylamino)methyl]-2-methoxybenzylalcohol hydrochloride are thereby obtained as colorless prisms.

M.p. 210°–211° C.

Analysis calculated for $C_{22}H_{32}O_5NCl$ C, 62.04; H, 7.57; N, 3.29; Found: C, 62.11; H, 7.44; N, 3.48.

EXAMPLE 19

(1) 1.31 g of 2-benzyloxyphenylglyoxal hydrate are dissolved in 3.5 ml of dimethylsulfoxide, and 0.97 g of α,α-dimethyl-3,4-methylenedioxyphenethylamine are added thereto. The mixture is stirred at 23° C. for 45 minutes, whereby a solution of α-(α,α-dimethyl-3,4-methylenedioxyphenethylimino)-2-benzyloxyacetophenone in dimethylsulfoxide is obtained.

(2) 9 ml of ethanol are added to the α-(α,α-dimethyl-3,4-methylenedioxyphenethylimino)-2-benzyloxyacetophenone solution obtained in paragraph (1), and 0.28 g of sodium borohydride are added thereto under ice-cooling. The mixture is stirred at room temperature for 3 hours. After the reaction, the reaction mixture is evaporated to remove the solvent. The residue is dissolved in ethyl acetate, and the solution is washed with water, dried and then evaporated to remove the solvent. The resultant caramel (2.2 g) is dissolved in ethanol containing 0.5 g of oxalic acid, and the solution is allowed to stand. The crystalline precipitates are collected by filtration, and then washed with ether. 1.8 g of α-[(α,α-dimethyl-3,4-methylenedioxyphenethylamino)-methyl]-2-benzyloxybenzylalcohol ½ oxalate are thereby obtained as colorless needles. M.p. 207°–208° C. (decomp.) The product is recrystallized from methanol, whereby said product decomposes at 211° C.

Analysis calculated for $C_{27}H_{30}O_6N$ C, 69.81; H, 6.51; N, 3.01; Found: C, 69.64; H, 6.52; N, 2.99.

EXAMPLE 20

A mixture of 1.2 g of α-[(α,α-dimethyl-3,4-methylenedioxyphenethylamino)methyl]-2-benzyloxybenzylalcohol ½ oxalate, 0.23 g of oxalic acid, 0.4 g of 10% palladium-carbon and 30 ml of 95% aqueous methanol is shaken at room temperature in hydrogen gas atmosphere under atmospheric pressure. After the uptake of hydrogen is completed, insoluble materials are removed by filtration, and the filtrate is condensed. The residue is dissolved in water, and the aqueous solution is allowed to stand. The crystalline precipitates are collected by filtration, and then washed with ethanol. 0.85 g of α-[(α,α-dimethyl-3,4-methylenedioxyphenethylamino)methyl]-2-hydroxybenzylalcohol ½ oxalate are thereby obtained as colorless needles. M.p. 210°–211° C. (decomp.) The product is recrystallized from 50% aqueous methanol, whereby said product decomposes at 211°–212° C.

Analysis calculated for $C_{20}H_{24}O_6N$ C, 64.15; H, 6.46: N, 3.74; Found: C, 64.31; H, 6.35; N, 3.84.

EXAMPLE 21

(1) A mixture of 590 mg of 2-methoxyphenylglyoxal hydrate, 500 mg of α,α-dimethyl-3,4-methylenedioxyphenethylamine and 1.5 ml of dimethylsulfoxide is stirred at room temperature for 45 minutes, whereby a solution of α-(α,α-dimethyl-3,4-methylenedioxyphenethylimino)-2-methoxyacetophenone in dimethylsulfoxide is obtained.

(2) 5 ml of ethanol are added to the α-(α,α-dimethyl-3,4-methylenedioxyphenethylimino)-2-methoxyacetophenone solution obtained in paragraph (1), and 200 mg of sodium borohydride are added thereto under ice-cooling. The mixture is stirred at room temperature for 3 hours. After the reaction, the reaction mixture is evaporated to remove the solvent. The residue is dissolved in ethyl acetate, and the solution is washed with water, dried and then evaporated to remove the solvent. The resultant caramel (980 mg) is dissolved in ethyl acetate, and 2 ml of ethanol containing oxalic acid (260 mg/2 ml) are added thereto. The mixture is allowed to stand, and the crystalline precipitates are collected by filtration and then washed with ethyl acetate. The crystals (660 mg) thus obtained is converted into its free base, and said free base is dissolved in ethanol. 210 mg of succinic acid are added to the solution, and said solution is allowed to stand. The crystalline precipitates are collected by filtration, and then washed with ethanol. 550 mg of α-[(α,α-dimethyl-3,4-methylenedioxyphenethylamino)methyl]-2-methoxybenzylalcohol ½ succinate are thereby obtained as colorless needles. M.p. 143°–145° C. The product is recrystallized from ethanol, whereby said product melts at 144°–145° C.

Analysis calculated for $C_{22}H_{28}O_6N$ C, 65.65; H, 7.01; N, 3.48; Found: C, 65.48; H, 7.23; N, 3.62.

EXAMPLE 22

(1) A mixture of 700 mg of 2-n-butoxyphenylglyoxal hydrate, 500 mg of α,α-dimethyl-3,4-methylenedioxyphenethylamine and 1.5 ml of dimethylsulfoxide is stirred at room temperature for 45 minutes, whereby a solution of α-(α,α-dimethyl-3,4-methylenedioxyphenethylimino)-2-n-butoxyacetophenone in dimethylsulfoxide is obtained.

(2) 5 ml of ethanol are added to the α-(α,α-dimethyl-3,4-methylenedioxyphenethylimino)-2-n-butoxyacetophenone solution obtained in paragraph (1), and 200 mg of sodium borohydride are added thereto under ice-cooling. The mixture is stirred at 20° C. for 3 hours. After the reaction, the reaction mixture is evaporated to remove the solvent. The residue is dissolved in ethyl acetate, and the solution is washed with water, dried and then evaporated to remove the solvent. The caramel thus obtained and 116 mg of oxalic acid are dissolved in ethanol, and the solution is allowed to stand. The crystalline precipitates are collected by filtration, washed with ethanol and then recrystallized from ethanol. 690 mg of α-[(α,α-dimethyl-3,4-methylenedioxyphenethylamino)methyl]-2-n-butoxybenzylalcohol ½ oxalate are thereby obtained as colorless needles.

M.p. 186°–187° C. (decomp.)

Analysis calculated for $C_{24}H_{32}O_6N$ C, 66.95; H, 7.49; N, 3.25; Found: C, 66.96; H, 7.32; N, 3.28.

EXAMPLE 23

(1) A mixture of 530 mg of 2-chlorophenylglyoxal hydrate, 500 mg of α,α-dimethyl-3,4-methylenedioxyphenethylamine and 1.5 ml of dimethylsulfoxide is stirred at room temperature for 45 minutes, whereby a solution of α-(α,α-dimethyl-3,4-methylenedioxyphenethylimino)-2-chloroacetophenone in dimethylsulfoxide is obtained.

(2) 5 ml of ethanol are added to the α-(α,α-dimethyl-3,4-methylenedioxyphenethylimino)-2-chloroacetophenone solution obtained in paragraph (1), and 200 mg of sodium borohydride are added thereto under ice-cooling. The mixture is stirred at 20° C. for 3 hours. After the reaction, the reaction mixture is evaporated to remove the solvent. The residue is dissolved in ethyl acetate, and the solution is washed with water, 10% hydrochloric acid and a saturated sodium chloride solution, successively. The washed solution is dried and then evaporated to remove the solvent, and the residue is crystallized with a mixture of ethyl acetate and ethanol. 690 mg of α-[(α,α-dimethyl-3,4-methylenedioxyphenethylamino)methyl]-2-chlorobenzylalcohol hydrochloride are thereby obtained as colorless prisms. M.p. 166°–168° C. The product is recrystallized from a mixture of ethanol and ether, whereby said product melts at 168°–171° C.

Analysis calculated for $C_{19}H_{23}O_3NCl_2$: C, 59.38; H, 6.03; N, 3.65; Found: C, 59.48; H, 6.05; N, 3.69.

What we claim is:
1. A benzylalcohol derivative of the formula:

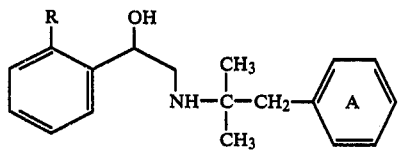

wherein R is hydroxy, benzyloxy, alkoxy of one to 4 carbon atoms or halogen, and Ring A is monomethoxyphenyl, dimethoxyphenyl, trimethoxyphenyl or 3,4-methylenedioxyphenyl, or a pharmaceutically acceptable acid addition salt thereof.

2. The compound of claim 1, in which R is hydroxy, benzyloxy, methoxy, n-butoxy or chlorine, and Ring A is 4-methoxyphenyl, 3,4-dimethoxyphenyl, 2,3,4-trimethoxyphenyl or 3,4-methylenedioxyphenyl.

3. The compound of claim 2, in which Ring A is 4-methoxyphenyl, 3,4-dimethoxyphenyl or 2,3,4-trimethoxyphenyl.

4. The compound of claim 2, in which Ring A is 3,4-dimethoxyphenyl, 2,3,4-trimethoxyphenyl or 3,4-methylenedioxyphenyl.

5. The compound of claim 2, in which Ring A is 4-methoxyphenyl, 3,4-dimethoxyphenyl or 3,4-methylenedioxyphenyl.

6. The compound of claim 2, in which Ring A is 4-methoxyphenyl or 3,4-dimethoxyphenyl.

7. The compounds of claim 2, in which Ring A is 3,4-dimethoxyphenyl or 2,3,4-trimethoxyphenyl.

8. The compound of claim 2, in which Ring A is 4-methoxyphenyl or 2,3,4-trimethoxyphenyl.

9. The compound of claim 2, in which Ring A is 4-methoxyphenyl.

10. The compound of claim 2, in which Ring A is 3,4-dimethoxyphenyl.

11. The compound of claim 2, in which Ring A is 2,3,4-trimethoxyphenyl.

12. The compound of claim 2, in which Ring A is 3,4-methylenedioxyphenyl.

13. The compound of claims 2 or 3, in which R is hydroxy, methoxy, n-butoxy or chlorine.

14. The compound of claims 2 or 3, in which R is hydroxy.

15. The compound of claims 2 or 3, in which R is benzyloxy.

16. The compound of claims 2 or 3, in which R is methoxy.

17. The compound of claims 2 or 3, in which R is n-butoxy.

18. The compound of claims 2 or 3, in which R is chlorine.

19. The compound of claim 3, in which R is benzyloxy, methoxy or n-butoxy.

20. The compound of claim 3, in which R is hydroxy, benzyloxy or chlorine.

21. The compound of claim 3, in which R is benzyloxy, methoxy or chlorine.

22. The compound of claims 6, 7 or 8, in which R is benzyloxy or methoxy.

23. The compound of claims 6, 7 or 8, in which R is methoxy or chlorine.

24. The compound of claims 6, 7, 8 or 10, in which R is benzyloxy or chlorine.

25. The compound of claim 19, in which Ring A is 4-methoxyphenyl.

26. The compound of claim 20, in which Ring A is 3,4-dimethoxyphenyl.

27. The compound of claim 21, in which Ring A is 2,3,4-trimethoxyphenyl.

28. The compound of claim 25 which is α-[(α,α-dimethyl-4-methoxyphenethylamino)methyl]-2-benzyloxybenzylalcohol or a pharmaceutically acceptable acid addition salt thereof.

29. The compound of claim 26 which is α-[(α,α-dimethyl-3,4-dimethoxyphenethylamino)methyl]-2-hydroxybenzylalcohol or a pharmaceutically acceptable acid addition salt thereof.

30. The compound of claim 26 which is α-[(α,α-dimethyl-3,4-dimethoxyphenethylamino)methyl]-2-benzyloxybenzylalcohol or a pharmaceutically acceptable acid addition salt thereof.

31. The compound of claim 26 which is α-[α,α-dimethyl-3,4-dimethoxyphenethylamino)methyl]-2-chlorobenzylalcohol or a pharmaceutically acceptable acid addition salt thereof.

32. The compound of claim 27 which is α-[(α,α-dimethyl-2,3,4-trimethoxyphenethylamino)methyl]-2-benzyloxybenzylalcohol or a pharmaceutically acceptable acid addition salt thereof.

33. The compound of claim 27 which is α-[(α,α-dimethyl-2,3,4-trimethoxyphenethylamino)methyl]-2-methoxybenzylalcohol or pharmaceutically acceptable acid addition salt thereof.

34. The compound of claim 27 which is α-[(α,α-dimethyl-2,3,4-trimethoxyphenethylamino)methyl]-2-chlorobenzylalcohol or a pharmaceutically acceptable acid addition salt thereof.

35. A blood-sugar lowering composition comprising an amount of the compound of claim 1 sufficient to provide an effective amount of said compound in the body of a warm-blooded animal when administered thereto, and a pharmaceutically acceptable carrier.

36. An anti-agglomerating agent comprising an amount of the compound of claim 1 sufficient to provide an effective amount of said compound in the body of a warm-blooded animal when administered thereto, and a pharmaceutically acceptable carrier.

* * * * *